(12) United States Patent
Huber et al.

(10) Patent No.: US 11,413,113 B2
(45) Date of Patent: Aug. 16, 2022

(54) HOLDING DEVICE, MEDICAL SYSTEM AND METHOD FOR POSITIONING A MEDICAL INSTRUMENT

(71) Applicant: KARL STORZ SE & Co. KG, Tuttlingen (DE)

(72) Inventors: Florian Huber, Tuttlingen (DE); Barbara Lettner, Tuttlingen (DE); Bernhard Glöggler, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 17/524,847

(22) Filed: Nov. 12, 2021

(65) Prior Publication Data

US 2022/0151728 A1 May 19, 2022

(30) Foreign Application Priority Data

Nov. 18, 2020 (DE) ...................... 10 2020 130 493.5

(51) Int. Cl.
*A61B 90/50* (2016.01)
*A61B 17/00* (2006.01)

(52) U.S. Cl.
CPC ........ *A61B 90/50* (2016.02); *A61B 17/00234* (2013.01); *A61B 2090/508* (2016.02)

(58) Field of Classification Search
CPC ... A61B 90/50; A61B 2090/508; A61B 90/10; A61B 34/30; A61B 34/32; A61B 34/35;
(Continued)

(56) References Cited

U.S. PATENT DOCUMENTS 5,372,147 A * 12/1994 Lathrop, Jr. ........... A61B 34/30
                                                                   600/230
2011/0150564 A1   6/2011 Stefan et al.
(Continued)

FOREIGN PATENT DOCUMENTS

DE          10307054 A1    9/2004
DE       102009060494 A1    6/2011
(Continued)

OTHER PUBLICATIONS

European Search Report for corresponding European Patent Application No. 21207709.3, dated Apr. 13, 2022.
(Continued)

*Primary Examiner* — Kathleen S Holwerda
(74) *Attorney, Agent, or Firm* — Jason H. Vick; Sheridan Ross, PC

(57) ABSTRACT

The disclosure relates to a holding device (12) for medical instruments (14) having a proximal base (20) for mounting on a frame (16), said base comprising a first joint (30), having a distal instrument holder (22) which comprises a second joint (32), having at least two sliding elements (52, 54, 58) between the base (20) and the instrument holder (22), and having at least two clamping elements (138, 140, 142, 144) which can be actuated by at least one transfer element (84, 86, 88), which can be operated jointly in a clamped stated and a released state, and which are designed to lock joints of the holding device (12) in the clamped state, wherein the at least two sliding elements (52, 54, 58) form a sliding joint (24) and can be displaced translationally relative to each other along a longitudinal axis (132), and wherein the at least two sliding elements (52, 54, 58) are telescopable relative to each other and coupled non-rotationally with each other. The disclosure also relates to a
(Continued)

medical system, a use of a holding device, as well as a method for positioning a medical instrument.

19 Claims, 5 Drawing Sheets

(58) Field of Classification Search
CPC ......... A61B 34/37; A61B 34/70; A61B 34/71; A61B 17/00234
See application file for complete search history.

(56) References Cited

U.S. PATENT DOCUMENTS

| | | | | |
|---|---|---|---|---|
| 2013/0247919 | A1* | 9/2013 | Chauvette | A61B 90/50 128/845 |
| 2016/0120611 | A1* | 5/2016 | Lohmeier | A61B 90/50 606/130 |

FOREIGN PATENT DOCUMENTS

| | | |
|---|---|---|
| DE | 102016108270 A1 | 11/2017 |
| WO | WO 2012/075571 A1 | 6/2012 |

OTHER PUBLICATIONS

German Office Action (Including Translation) for corresponding German Application No. 10 2020 130 493.5, dated Jul. 13, 2021.

* cited by examiner

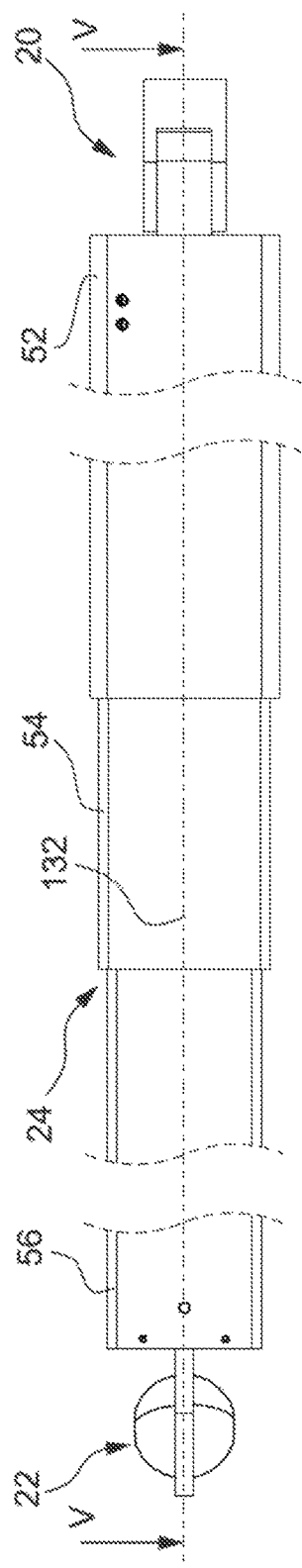
Fig. 4
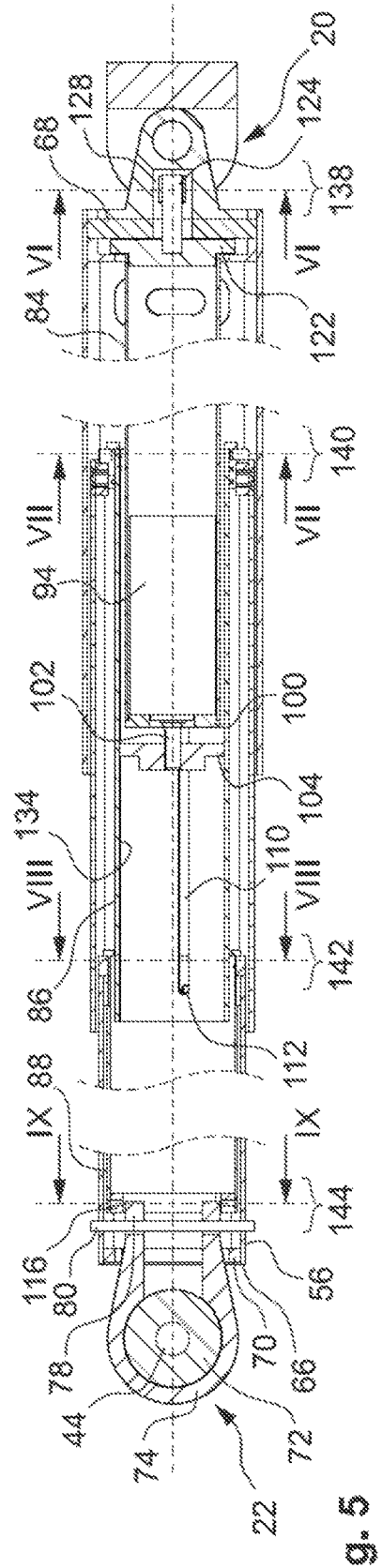
Fig. 5
Fig. 6
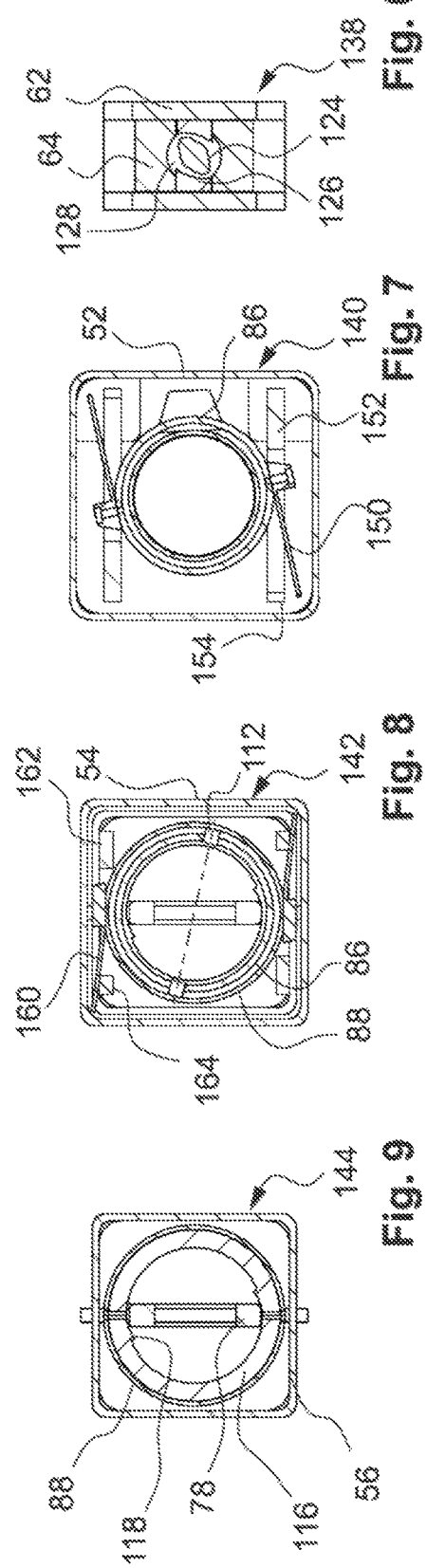
Fig. 7
Fig. 8
Fig. 9

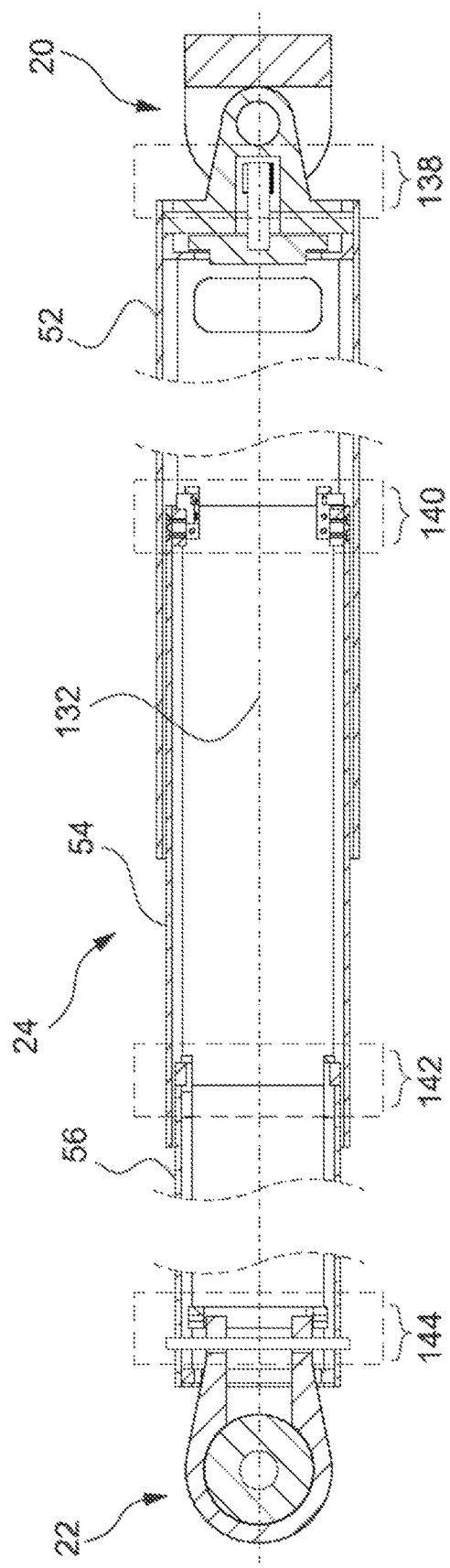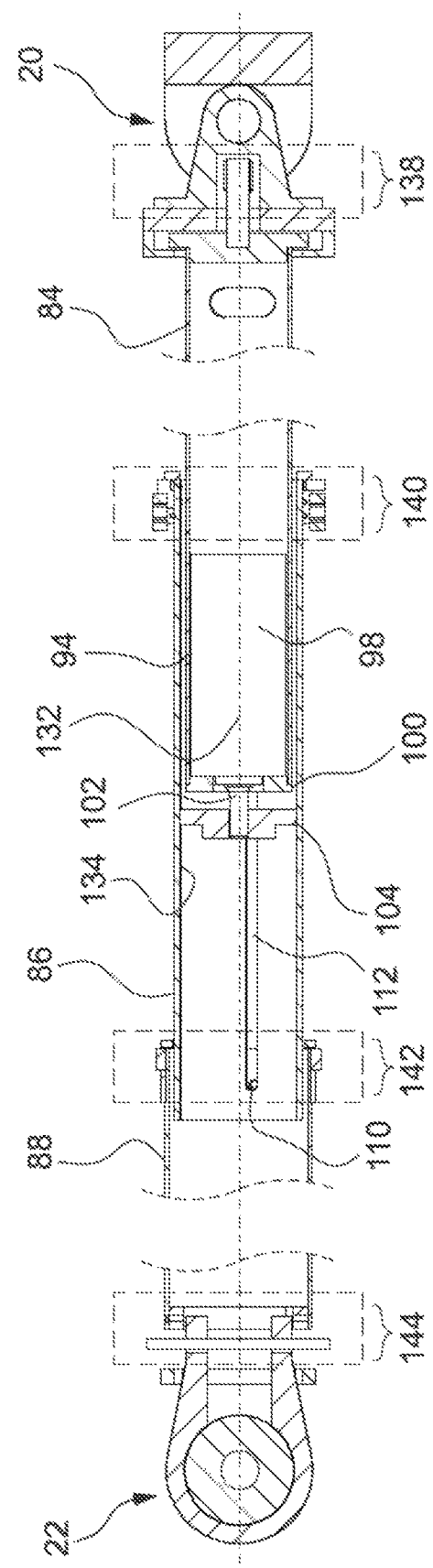
Fig. 10
Fig. 11

HOLDING DEVICE, MEDICAL SYSTEM AND METHOD FOR POSITIONING A MEDICAL INSTRUMENT

CROSS-REFERENCE TO RELATED APPLICATIONS

This application claims the benefit under 35 U.S.C. 119(a) to German Patent Application No. 10 2020 130 493.5, filed 18 Nov. 2020, the disclosure of which is incorporated herein by reference in its entirety.

BACKGROUND

The present disclosure relates to a holding device for medical instruments, particularly endoscopic instruments.

A holding and guiding system for a medical instrument, particularly an endoscope, is known from DE 103 07 054 A1, said system having at least one guide arm to which the medical instrument is coupled, wherein the guide arm is movably mounted by means of two holding rods to form a kinematic tripod.

In the medical field, there are established instruments that are used in a handheld and/or hand-guided manner. These include, for example, hand-guided endoscopic instruments that can be inserted through a trocar into the body of a patient. However, instruments are also known, for example observation instruments, which are positioned in relation to the patient and then remain fixed for at least some time. Mixed forms are conceivable, including instruments that are repositioned from time to time during a procedure.

Medical instruments, specifically also hand-guided endoscopic instruments, are occasionally accommodated on stands or the like, and positioned and oriented in relation to the patient. One advantage of this approach is that the medical specialist (the surgeon, for example) then has both hands free. However, frames and stands for medical instruments can be quite complex and elaborate, and can comprise a plurality of operating elements. This results in an adjustment being frequently associated with a great deal of effort. Furthermore, it shall be noted that medical procedures are frequently conducted under increased hygiene requirements (clean room conditions, sterilization, and so on).

Prior art also describes so-called surgical robots that can control all degrees of freedom of a medical instrument in a motorized manner via an operating console. In other words, the surgeon no longer has to interact directly with the patient. Surgical robots are very cost-intensive and are only used to a limited extent in actual practice to date.

In addition, for certain applications, it is no longer absolutely necessary to provide a plurality of degrees of freedom of movement for held instruments. It is often sufficient for one to be able to position a grasped instrument, for example an endoscopic instrument, in an essentially free manner in a certain plane, and provide one or more pivoting degrees of freedom for the instrument at the desired position as necessary. The force for moving and orienting the instrument can be applied by the medical personnel, at least in certain applications. In such a case, the frame/stand can be locked when the desired position is reached.

For medical procedures, particularly in operations and other surgical procedures, an unobstructed view and unrestricted accessibility of the patient are extremely important to medical personnel. Therefore, it is generally desirable to avoid blocking or obstructing the immediate surgery site with cumbersome, bulky equipment.

With this in mind, the object of the present disclosure is to specify a holding device for medical instruments which permits picking up and positioning a medical instrument and provides suitable degrees of freedom for this purpose. In particular, the holding device is meant to allow positioning a medical device in a plane and to provide at least one pivoting axis for the instrument there. The holding device shall be simple to operate. The holding device shall allow one to manually position the instrument, at least in illustrative embodiments. To secure the positioned instrument, one shall be able to lock the holding device with little effort, at least in illustrative embodiments. Similarly, it is preferred if one can unlock the holding device in a simple manner to reposition or reorient the instrument.

Furthermore, the scope of the present disclosure shall specify a medical system having such a holding device, a corresponding use of a holding device for positioning a medical instrument as well as a corresponding method for positioning a medical instrument.

According to a first aspect, the present disclosure relates to a holding device for medical instruments, particularly endoscopic instruments, having the following:
  a proximal base, comprising a first joint, for mounting on a frame,
  a distal instrument holder that comprises a second joint,
  at least two sliding elements between the base and the instrument holder, and
  at least two clamping elements, which can be actuated by at least one transfer element, which can be jointly operated in a clamped state and a released state, and which are designed to lock joints of the holding device in the clamped state,
  wherein the at least two sliding elements form a sliding joint and can be displaced relative to each other along a longitudinal axis in a translational manner, and
  wherein the at least two sliding elements are telescopable relative to each other and are non-rotationally coupled to each other.

In this way, the object is achieved.

Specifically, according to the invention, a mechanism is provided which offers multiple degrees of freedom of movement which can be jointly locked or released. Handling is made easier. The effort for positioning and orienting the instrument can be reduced. The holding device is designed in a compact and space-saving manner.

The movable joints involve, for example, members of the first joint, the second joint and/or the sliding joint. "Jointly" means that multiple or all of the clamping elements can be actuated simultaneously to bring these into the clamped state or released state as needed, at least in illustrative embodiments.

Endoscopic instruments are instruments that are designed to be inserted through natural or artificially created openings in the body of a patient. Endoscopic instruments also include, for example, laparoscopic instruments, neurosurgical instruments and the like.

Within the meaning of the present disclosure, a distal element is an element which, when seen from a base or a frame of the holding device, faces the patient or patient support platform or is arranged closer to the patient than a proximal element. Within the meaning of the present invention, a proximal element is an element which, from the perspective of the patient or the patient support platform, faces the frame or is arranged closer to the frame than a distal element. Therefore, within the scope of the present disclosure, the terms "proximal" and "distal" are generally used within the scope of their conventional meaning in the field of medical technology. This shall not be understood as being restrictive.

Within the meaning of the present disclosure, "telescopable" includes, for example, a design in which at least two sliding elements are able to move into each other. A telescopable sliding joint can be moved between a retracted position and an extended position. For example, at least one clamping element is provided to lock the current position of the sliding joint as needed.

In the clamped state, the clamping elements impede or block the relative movements between adjoining elements, which are movable relative to each other in the released state. A form-fitting position-securing element is not necessarily required, at least in illustrative embodiments. In one illustrative embodiment, the clamping elements are designed to increase the friction between the adjoining elements in such a manner that a relative movement between these elements is possible only with a correspondingly high exertion of force. In this way, clamping/locking can be achieved. If the holding device is locked in the clamped state, the medical instrument is held on the instrument holder in a sufficiently firm manner.

According to one illustrative embodiment, the first joint is designed as a swivel joint. According to another illustrative embodiment, the second joint is designed as a ball joint. In this way, in addition to the sliding joint there is a swivel joint and possibly a ball joint. Together, the sliding joint and the swivel joint ensure that the holding device can place the instrument in a plane, for example parallel to the patient support platform. The approachable region results from the possible travel path of the sliding joint as well as the possible pivoting angle of the swivel joint. The ball joint allows pivoting movements of the instrument about the instrument holder, at least in illustrative embodiments.

It is understood that within the scope of the present disclosure the terms "first element," "second element" and the like do not specify any mandatory order or weighting, but are used primarily for the purpose of differentiation. Therefore, one can basically also conceive of embodiments that only have one of the elements, for example only the second element.

According to one illustrative embodiment, the holding device is designed to allow movements in a plane, particularly in a plane that is oriented parallel to a patient support platform. In this way, the instrument can be positioned at a desired location and fixed there in a desired orientation by using the ball joint. In one illustrative embodiment, the instrument can also be translationally displaced and positioned along its longitudinal axis in the ball joint.

According to one illustrative embodiment, between the first joint on the proximal base and a proximal sliding element, there is provided a clamping element that acts on the first joint, wherein between the second joint on the distal instrument holder, there is provided a clamping element that acts on the second joint.

According to another illustrative embodiment, the first joint comprises a receiving means and a pivot piece, which jointly define a pivot axis, wherein the first joint is assigned a proximal clamping element, which blocks or locks the first joint in a clamped state as needed. In this way, a given pivot state of the instrument holder can be fixed for positional stability. Preferably, this is accompanied by positional stability of the sliding joint in the given extended position.

According to one illustrative embodiment, the clamping element for the first joint comprises an eccentric that projects beyond the proximal sliding element as a proximal extension. The eccentric is coupled to a transfer element. According to one illustrative embodiment, the eccentric extends into a recess in the pivot piece, wherein in the clamped state the eccentric is rotated in the recess and acts on a plunger or a pressure piece in such a manner that the pivot piece and the receiving means are tensioned together and locked.

According to another illustrative embodiment, the second joint comprises a guide ball and a ball cup, particularly a ball cup designed in a yoke-like manner, wherein the guide ball has an instrument receiving means for holding the medical instrument, and wherein the second joint is assigned a distal clamping element that blocks or locks the second joint as needed in the clamped state.

In this way, the second joint can provide multiple pivoting degrees of freedom. These degrees of freedom of movement can be blocked/locked as needed using a clamping element. The guide ball comprises, for example, a recess that can receive a shaft of the instrument. In this way, another rotational degree of freedom can be provided as needed for rotating the instrument about its shaft, which can also be blocked/locked using the clamping element. The guide ball comprises a sufficiently elastic material for illustrative purposes.

According to another illustrative embodiment, the distal clamping element acts on the yoke-like ball cup to immobilize the guide ball relative to the ball cup. In this way, the degrees of freedom of the ball joint are blocked.

According to one illustrative embodiment, for the second joint, the clamping element comprises an inward-acting clamping ring, which is designed as a distal end of a distal transfer element and acts from the outside on two shanks of the yoke-like ball cup to press together the two side pieces. In this way, the guide ball in the ball cup is braced or blocked. The clamping ring can also be referred to as an eccentric ring. The clamping ring is provided with an eccentric contour to place a load on the two shanks in a clamped state to block the guide ball.

In an illustrative embodiment, a distal section of the first joint, for example the pivot piece of the swivel joint, is non-rotationally attached to the proximal sliding element. In an illustrative embodiment, a proximal section of the second joint, for example the cup of the ball joint, is non-rotationally attached to the distal sliding element. This results in a closed, integrated design. Various elements are covered and protected by the sliding elements.

According to another illustrative embodiment, a common drive for the at least two clamping elements is provided, which simultaneously activates the at least two clamping elements. According to another illustrative embodiment, one single drive is provided. In an illustrative embodiment, a single drive is provided that simultaneously activates all clamping elements. In an illustrative embodiment, the clamping elements are activated synchronously/simultaneously.

In an illustrative embodiment, the drive is a manually operated drive. In an illustrative embodiment, the drive is a motor drive, particularly an electric motor drive. It is understood that, basically, the motor drive can be formed by a pneumatic or fluidic drive. In an illustrative embodiment, a switch is provided for operating the motor. The switch may be arranged directly at the holding device. However, the switch can also be at a distance from the holding device. In an illustrative embodiment, the switch has at least two states that correspond to the released state and the clamped state. In an illustrative embodiment, the switch has at least three states, which pertain to activation of the drive in a first rotational direction having a first direction of rotation, activation of the drive in an opposite second rotational direction and deactivation of the drive.

In an illustrative embodiment, the drive comprises a motor that is arranged on one of the sliding elements. In an illustrative embodiment, the motor is arranged on a proximal sliding element adjoining the first joint, wherein the proximal sliding element connects at least to a distal sliding element. This results in a favorable mass distribution or mass inertia, at least in illustrative embodiments. Components of the holding device which are larger and/or heavier are provided closer to the proximal base than to the distal instrument holder.

According to another illustrative embodiment, the drive comprises a drive shaft that interacts with at least one of the clamping elements, wherein the drive also has a bearing piece which absorbs a resulting counter-torque when the drive shaft is driven, and wherein the bearing piece interacts with at least one of the other clamping elements. In other words, the drive torque and the resulting counter-torque, with which a drive affixed to the frame would brace itself on the frame, are used to drive sliding elements in a counter-rotating manner.

In an illustrative embodiment, the drive is mounted in a "floating" manner inside the at least two sliding elements. In other words, the drive is not necessarily affixed to a frame or a base. If necessary, this occurs indirectly.

According to another illustrative embodiment, the drive shaft is oriented parallel to the longitudinal axis, wherein the bearing piece is coupled to a proximal clamping element that is assigned to the first joint. In an illustrative embodiment, the drive shaft extends toward the distal instrument holder. The bearing piece can be coupled directly or indirectly to the proximal clamping element.

According to another illustrative embodiment, the drive is coupled to at least two telescopable transfer elements, wherein the number of the transfer elements is matched to the number of slide elements, and wherein the transfer elements transfer a rotational movement induced by the drive to place the at least two clamping elements into the clamped state or the released state. In an illustrative embodiment, the number of sliding elements matches the number of transfer elements. The transfer elements, which can also be referred to as transmission elements, are used to transfer the drive movement of the drive torque.

In an illustrative embodiment, the sliding element and the transfer elements are jointly telescopable at the same time. In other words, a user can move the sliding elements to extend the holding device. With the translational movement of the sliding elements, the transfer elements are also moved translationally. In other words, the transfer elements are carried along by the sliding elements during the translational movement, at least in illustrative embodiments.

In an illustrative embodiment, the telescoping movement is generated manually if the clamping elements are in the released state.

In an illustrative embodiment, the transfer elements are arranged inside the sliding elements. In an illustrative embodiment, the transfer elements are tube sections, particularly cylindrical tube sections having an annular profile. In an illustrative embodiment, the cross-sections of the transfer elements are adapted to each other in such a manner that the transfer elements can be telescoped.

In an illustrative embodiment, the sliding elements form an outer shell having anti-rotation means, wherein the transfer elements form an at least partially rotatable inner shell.

According to another illustrative embodiment, the drive is coupled to two adjoining transfer elements in such a manner that the adjoining transfer elements are rotated in opposite directions when the drive moves. In this way, when there is a "floating" bearing, the drive can be braced by the counter-rotating transfer elements, wherein a transfer element is driven via the (output-side) drive shaft and another transfer element is driven via the bearing piece (coupled to the drive housing).

In an illustrative embodiment, the bearing piece of the drive is coupled to a first transfer element, wherein the drive shaft is coupled to an adjoining second transfer element. In this way, the drive torque is first introduced into the second transfer element. The counter-torque is not introduced in a part fixed to the frame but in the first transfer element. In this way, the two transfer elements are rotated in opposite directions.

In an illustrative embodiment, the drive is thus not mounted in a manner fixed to the frame, but coupled indirectly to the base. In this way, the counter-torque can also be used for generating movement. In an illustrative embodiment, the drive tensions two adjoining transfer elements against each other.

According to another illustrative embodiment, the sliding elements and the transfer elements are each designed as hollow profile bodies, wherein the transfer elements are arranged inside the sliding elements, and wherein the drive has a cartridge-like housing that is non-rotationally coupled to one of the transfer elements, particularly to a proximal transfer element. In this way, an integrated design is obtained. Various movable components of the holding device are protected by the sliding elements.

According to another illustrative embodiment, three or more transfer elements are provided, of which at least two adjoining transfer elements, particularly two distal transfer elements, are coupled to each other in a non-rotational manner and can be displaced translationally relative to each other. In this way, the transfer elements can take part in the telescoping movement of the sliding elements and simultaneously contribute to locking or releasing the sliding elements using only one drive or one drive movement.

In an illustrative embodiment, one of the two transfer elements has at least one axially extending guide, for example an elongated hole, wherein the other of the two transfer elements has a corresponding guide element, for example a guide bolt or guide pin, wherein the guide element is movably mounted in the guide.

According to another illustrative embodiment, the holding device comprises at least three sliding elements which form a sliding joint and are telescopable, wherein cross-sectional profiles of the sliding elements are graduated and become smaller starting from the proximal base to the distal instrument holder. This is beneficial for rigidity, mass inertia and mass distribution.

According to another illustrative embodiment, the at least two sliding elements have a box profile, particularly a square profile, and wherein the box profiles of the sliding elements are adapted to each other in such a manner that the sliding elements can be telescoped along the longitudinal axis and are coupled to each other in a non-rotational manner. The cross-sectional profile of the sliding elements may be a square profile in the form of a rectangular profile or quadrate profile, for example. In principle, other designs are conceivable. Illustrative designs include cross-sectional profiles that are non-circular, and thus have a non-rotational form.

According to another illustrative embodiment, there is arranged in each case a clamping element between two adjoining sliding elements. These may be clamping elements acting directly on the sliding elements. However, it is also conceivable to provide clamping elements which act indirectly to lock/fix in each case two adjoining clamping elements relative to each other. This can occur for example by interposing the transfer elements.

According to another illustrative embodiment, at least the clamping elements assigned to the sliding elements can be operated rotationally, wherein the corresponding clamping elements clamp the sliding elements having the at least one transfer element in a given translational position.

According to another illustrative embodiment, at least one of the clamping elements has an eccentric, wherein at least one eccentric is designed as a spring eccentric and/or has eccentric contours, and wherein given a relative rotation, the eccentric creates a form-fitting fastening between the at least one transfer element and the sliding element.

In other words, the eccentrics can interact, for example, with a non-rotation-symmetrical hollow profile of the sliding elements so that given a rotation of the interior eccentrics, a friction fit and/or a force fit is produced with the sliding elements. In this way, the sliding elements can be fixed relative to each other in their given translational position.

The eccentrics can be designed as pliable/elastic eccentrics which in a clamped state act on the sliding elements with a pre-tensioning force. However, it is also conceivable to use rigid eccentrics whose clamping effect is based primarily on friction.

According to another illustrative embodiment, the sliding elements have inside stops for the clamping elements, particularly for eccentrics of the clamping elements, wherein the stops define an end position for the rotation of the transfer elements in the clamped state of the clamping elements. In this way, "over-tightening" of the clamping elements can be avoided. For the clamping elements, there is preferably a defined stop for the released state and a defined stop for the clamped state. In this way, operation is unambiguous.

According to another illustrative embodiment, the sliding elements also have additional inside stops for the clamping elements, wherein the additional stops define an end position for the rotation of the transfer elements in the released state of the clamping elements.

According to another illustrative embodiment, the holding device has the following:
  exactly three telescopable sliding elements, comprising a proximal sliding element, a middle sliding element and a distal sliding element, which form a sliding joint, wherein the three sliding elements are coupled to each other in a non-rotational manner,
  exactly three telescopable transfer elements, comprising a proximal transfer element, a middle transfer element and a distal transfer element, which are arranged inside the sliding elements,
  a swivel joint, which forms the first joint on the proximal base,
  a ball joint, which forms the second joint of the distal instrument holder,
  a first clamping element, which is assigned to the swivel joint and is arranged between the proximal transfer element and the swivel joint,
  a second clamping element, which is arranged between the middle transfer element and the proximal sliding element,
  a third clamping element, which is arranged between the distal transfer element and the middle sliding element,
  a fourth clamping element, which is assigned to the ball joint and is arranged between the distal transfer element and the ball joint,
  wherein, in the clamped state, the four clamping elements lock the swivel joint, the sliding joint and the ball joint,
  wherein the four clamping elements can be jointly activated and deactivated, and
  wherein the four clamping elements can be controlled via a common drive to lock or release the swivel joint, the sliding joint and the ball joint simultaneously.

Activating comprises a blocking/locking. Deactivating comprises a disengaging or a releasing.

According to another aspect, the present disclosure relates to a medical system, particularly an endoscopic system, comprising a holding device according to one of the embodiments described herein as well as a medical instrument which is received on the distal instrument holder, wherein the medical instrument penetrates through the distal instrument holder, and wherein the medical instrument is movable along an instrument axis when a clamping element assigned to the second joint is in a released state.

The instrument axis is, for example, a longitudinal axis through an instrument shaft. In an illustrative embodiment, the medical instrument can be rotated about the longitudinal axis of the instrument shaft or can be moved along the longitudinal axis when the clamping element assigned to the second joint is in a released state.

According to another aspect, the present disclosure relates to a use of a holding device according to one of the embodiments described herein for positioning a medical instrument, particularly an endoscopic instrument.

According to another aspect, the present disclosure relates to a method for positioning a medical instrument, particularly an endoscopic instrument, having the following steps:
  Providing a holding device according to one of the embodiments described herein,
  Attaching a medical instrument to the distal instrument holder,
  Positioning the holding device with the instrument in the released state of the at least two clamping elements, and
  Locking the holding device in the clamped state of at least two clamping elements.

In an illustrative embodiment of the method, the step of providing the holding device also comprises attaching the holding device, particularly the base of the holding device, to a frame, for example a patient support platform.

In an illustrative embodiment, the method is restricted for purposes other than methods for surgical or therapeutic treatment of the human or animal body and diagnostic procedures that are undertaken on the human or animal body. Similarly, in an illustrative embodiment, the use is restricted to purposes other than methods for the surgical or therapeutic treatment of the human or animal body and diagnostic procedures that are undertaken on the human or animal body.

For example, this may involve the positioning of an observation instrument which monitors the body from the outside, particularly without further interaction with the body.

It is understood that the aforementioned characteristics and those still to be explained below can be used not only in the respective indicated combination, but also in other combinations or when considered alone, without departing from the scope of the present disclosure.

BRIEF DESCRIPTION OF THE DRAWINGS

Additional features and advantages of the invention emerge from the following description and explanation of various illustrative embodiments with reference to the drawings.

FIG. 4 depicts a broken side view of the holding device according to FIG. 2;

FIG. 5 depicts a broken cross-sectional view of the holding device according to FIG. 4 along line V-V in FIG. 4;

FIGS. 6-9 depict frontal side views of the holding device according to FIG. 5 along lines VI-VI (FIG. 6), VII-VII (FIG. 7), VIII-VIII (FIG. 8) and IX-IX (FIG. 9) in FIG. 5;

FIG. 10 depicts another broken side view based on the illustration according to FIG. 5, wherein elements are hidden for illustrative purposes;

FIG. 11 depicts another broken side view based on the illustration according to FIG. 5, wherein elements are hidden for illustrative purposes;

DETAILED DESCRIPTION

Figure 1:
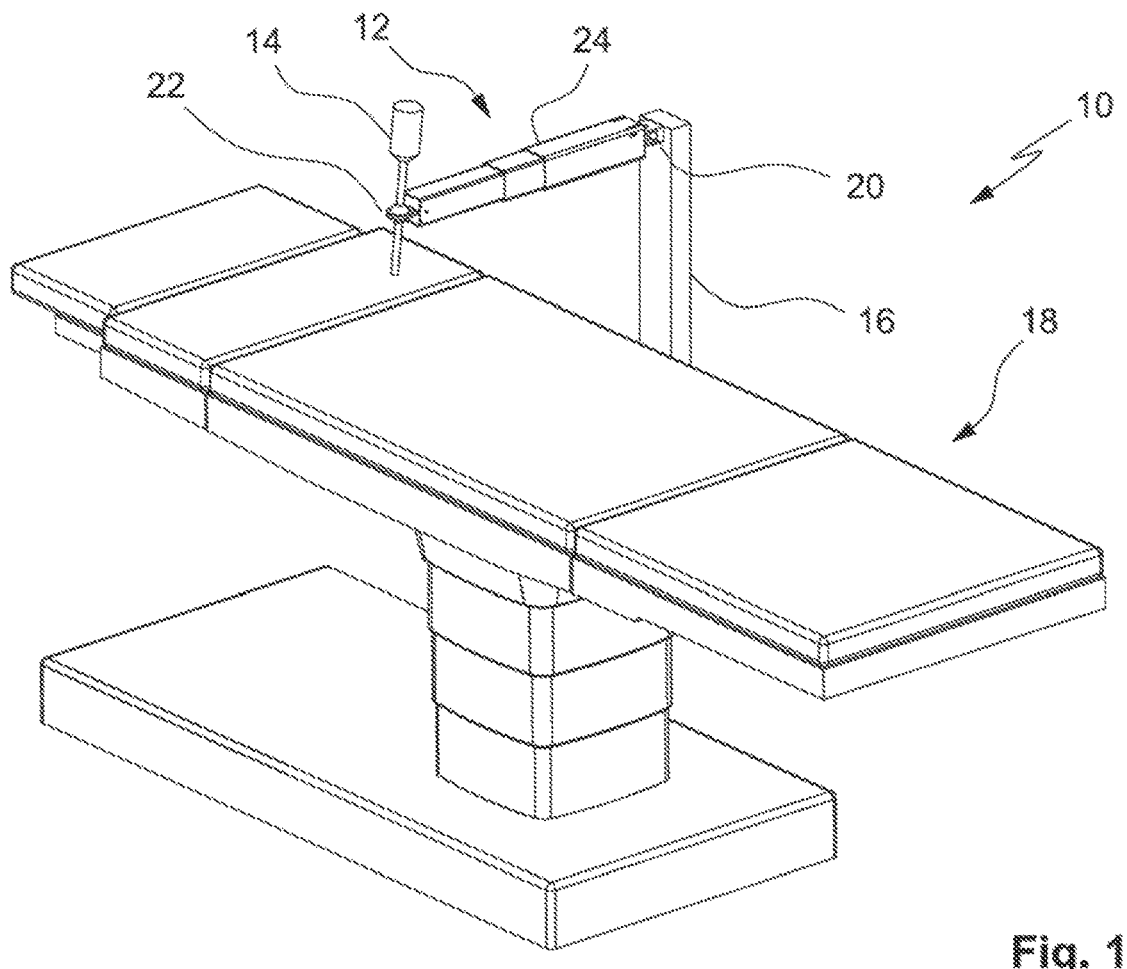
FIG. 1 depicts a perspective view of a medical system having a holding device.

By means of a perspective view, FIG. 1 depicts an embodiment of a medical system identified as 10. The medical system 10 has a holding device 12 that carries a medical instrument 14. The holding device 12 is arranged on a patient support platform 18 by means of a frame 16. In the embodiment, the holding device 12 is used to position and orient the instrument 14 relative to the patient support platform 18.

The medical instrument 14 is, for example, an endoscopic instrument that is designed to be inserted into the body of a patient. In other embodiments, the medical instrument 14 is an instrument that is placed outside the body of a patient during a medical procedure. In other words, the medical instrument 14 may be, for example, an endoscopic observation instrument or an exoscope. An exoscope is an observation element for observing an object plane from outside the body, and thus at a working distance that is typically greater than the working distance of an endoscopic observation instrument.

In the embodiment depicted in FIG. 1, the holding device 12 with the instrument 14 received on it can be positioned in a plane parallel to the patient support platform 18. For this purpose, the holding device 12 has a proximal base 20 that is attached to the frame 16. On the opposite end of the holding device 12, a distal instrument holder 22, which carries the instrument 14, is provided. In other words, the holding device 12 extends between a proximal end and a distal end. The holding device 12 also comprises a sliding joint 24, which is arranged between the proximal base 20 and the distal instrument holder 22.

Figure 2:
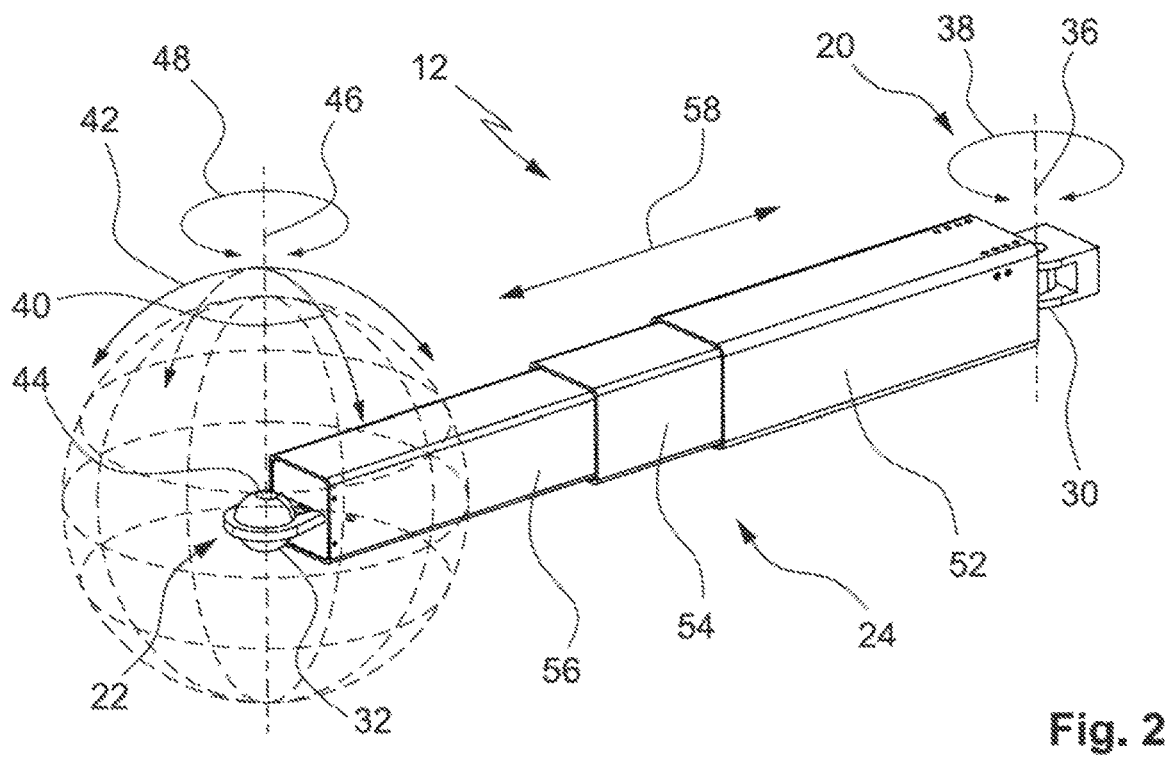
FIG. 2 depicts a perspective view of an illustrative embodiment of a holding device.

With further reference to FIG. 2, degrees of freedom of movement of the holding device 12 are depicted. The proximal base 20 has a first joint (proximal joint) 30, which defines a pivot axis 36. In other words, the first joint 30 can also be referred to as a pivot joint. A curved double arrow labeled 38 depicts a possible rotation/pivot movement of the holding device 12 relative to the frame 16 (cf. FIG. 1). In this way, the holding device 12 with the instrument 14 can be pivoted about the pivot axis 36, similar to an extension arm.

The distal instrument holder 22 has a second joint (distal joint) 32, which allows pivot movements of the instrument 14. In the embodiment according to FIG. 2, the second joint 32 is designed as a ball joint. Curved double arrows 40, 42 depict conceivable pivot movements of the instrument 14, which are made possible by the second joint 32. The second joint 32 comprises an instrument receiving means 44, which is designed for example as a receiving hole for the instrument 14. In the embodiment according to FIG. 2, the instrument receiving means 44 defines an instrument axis 46 for the received instrument 14 (cf. FIG. 1). In an illustrative embodiment, the instrument 14 can be inserted into the instrument receiving means 44 with an instrument shaft and held there. In an illustrative embodiment, the instrument 14 in the instrument receiving means 44 can be rotated about the instrument axis 46 (cf. the rotation movement 48), which is depicted by a curved double arrow. Translational movements along the instrument axis 46 are also conceivable.

The sliding joint 24 extends between the first joint 30 and the second joint 32. In the embodiment, the sliding joint 24 comprises three sliding elements 52, 54, 56. It is understood that the sliding joint 24 may basically comprise two or more sliding elements, for example two, three, or four sliding elements. The sliding joint 24 allows a translational movement (cf. the double arrow 58 in FIG. 2). In other words, the sliding joint 24 allows an extension movement or retraction movement of the sliding elements 52, 54, 56.

All in all, the holding device 12 has at least three joints, specifically the first joint 30, the second joint 32 and the sliding joint 24 lying between them. The sliding joint 24 provides a translational movement. The first joint 30 designed in the embodiment as a swivel joint permits a pivot movement. The second joint 32 designed in the embodiment as a ball joint allows pivot movements about a plurality of axes. The joints 24, 30 are used for positioning the instrument holder 22 in a plane. The range in which positioning is possible is defined by the possible pivot angle of the swivel joint 30 and the stroke (travel path) of the sliding joint 24. The plane is oriented parallel to the patient support platform (FIG. 18), for example. In the embodiment, the joint 32 allows one to orient the instrument 14 held on the instrument holder 22. This can include pivot movements in the joint 32 designed as a ball joint. In illustrative embodiments, the instrument 14 can also be moved translationally in the instrument receiving means 44 and rotationally about the instrument axis 46.

In an illustrative embodiment, the instrument 14 is moved and oriented manually using the holding device 12. In other words, medical personnel can manually place and orient the instrument 14. In this embodiment, no separate drives for the degrees of freedom of movement of the joints 24, 30, 32 are required. It is understood that in principle designs are also conceivable in which positioning and orientation of the instrument 14 take place using motors/actuators. However, it has been shown that in many applications, manual orientation is absolutely sufficient.

However, an essential aspect is the ability to definitively lock or release the holding device 12. In a locked or blocked/impeded state of the holding device 12, the instrument 14 is positioned and oriented in a sufficiently secure manner. In other words, in this state a continuing movement of the instrument 14 and/or holding device 12 is prevented, or only possible by exerting a large amount of force. However, if the instrument 14 is now to be repositioned, or a new orientation of the instrument 14 is desired, the locked state (also referred to as clamped state) must be cleared so that the holding device 12 with the instrument 14 can be moved in the desired degrees of freedom. Therefore, it is advantageous if the locking and releasing of the holding device 12 can be achieved in a simple manner. Preferably, the user (operator) must perform only one action to lock or release the entire holding device 12.

The reference to FIGS. 3-12 as well as the further reference to FIGS. 1 and 2 explain illustrative embodiments of the holding device 12 in greater detail. Various aspects of the present disclosure deal with the simultaneous locking or releasing of the joints, 24, 30, 32.

Figure 3:
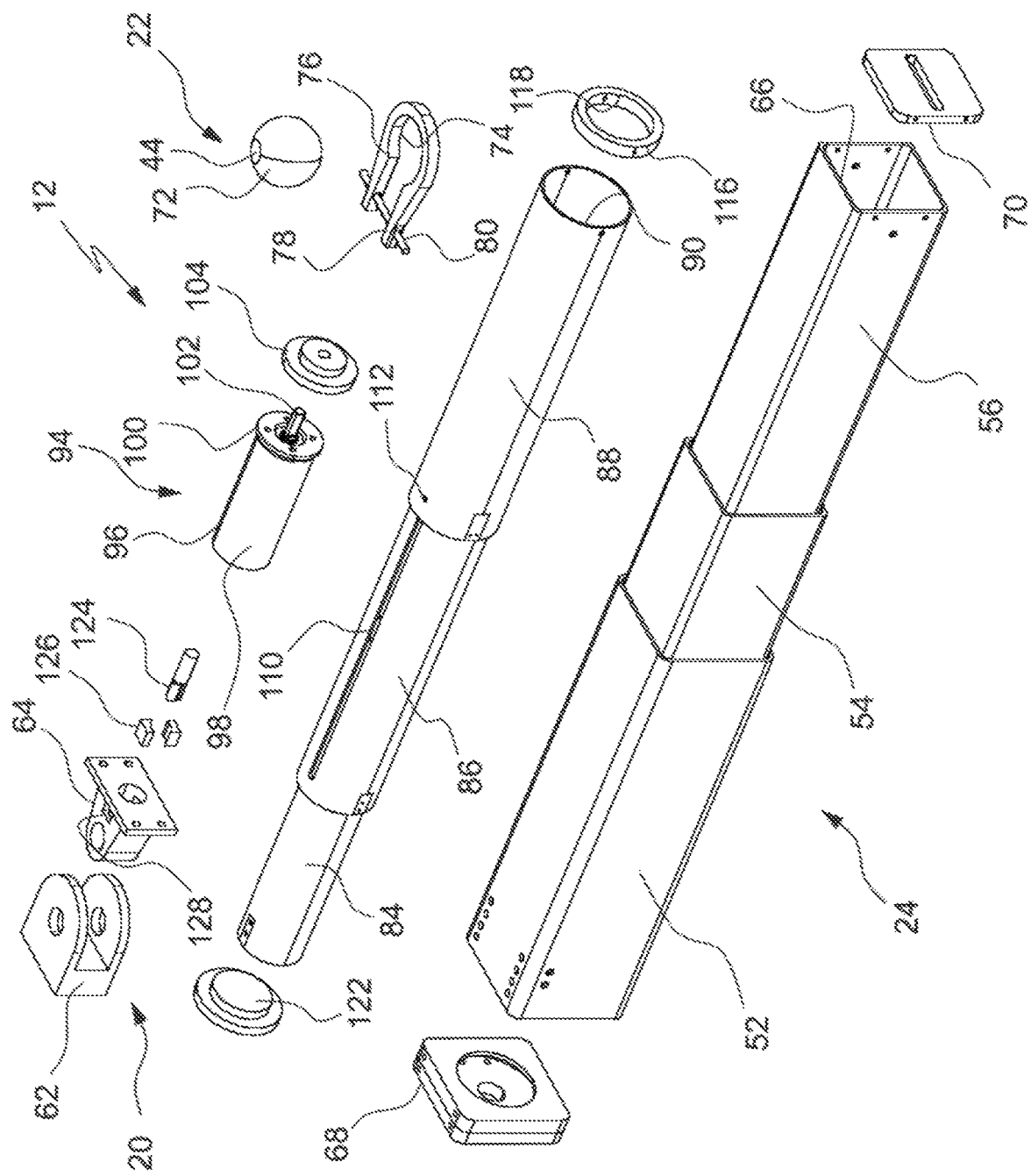
FIG. 3 depicts an exploded perspective view of the holding device according to FIG. 2.

By means of a perspective, exploded view, FIG. 3 depicts an illustrative detail design of the holding device 12 according to FIG. 2. FIGS. 4-11 supplement this illustration. FIG. 4 depicts a broken side view of the holding device 12 according to FIGS. 2 and 3. FIG. 5 depicts a corresponding cross-sectional view, wherein the sectional plane is indicated by the arrows V-V in FIG. 4. By means of the arrows VI-VI, VII-VII, VIII-VIII as well as IX-IX, FIGS. 6, 7, 8 and 9 depict front cross-sectional views transversely to the longitudinal extension of the holding device 12. FIGS. 10 and 11 are based on FIG. 5, wherein in each case various components of the holding device 12 are hidden for illustrative purposes.

The base 20 forming the first joint 30 has a receiving means 62 and a pivot piece 64, which is pivotably mounted at the receiving means 62. In the embodiment according to FIG. 1, the receiving means 62 is fastened to the frame 16. In FIG. 3, a bolt was omitted from the depiction for clarity's sake, said bolt connecting the receiving means 62 and the pivot piece 64.

The proximal base 20 is coupled to the sliding joint 24. The sliding joint 24 is formed of the sliding elements 52, 54, 56 as seen in the embodiment. The sliding elements 52, 54, 56 each have a profile body 66 having a cross-sectional profile. FIG. 3 pertains in each case to a square profile or rectangular profile. The profile bodies 66 of the sliding elements 52, 54, 56 are adapted to each other so that the sliding element 56 is arranged inside the sliding element 54, and the sliding element 54 is arranged inside the sliding element 52. This relates in each case to the cross-section of the respective profile body 66. In this way, the sliding elements 52, 54, 56 can plunge into each other or be moved translationally relative to each other between a retracted and an extended state. The sliding elements 52, 54, 56 are connected to each other in a non-rotational manner based on their profile body 66.

The pivot piece 64 of the proximal base 20 is connected to a proximal cap 68, which in turn is coupled to the proximal sliding element 52. In this way, in the depicted embodiment the sliding element 52 of the sliding joint 24 is securely connected to the pivot piece 64. Consequently, given a pivot movement between the pivot piece 64 and the receiving means 62, the sliding joint 24 is also pivoted. Provided on the distal end of the distal sliding element 56, there is a cap 70, which is connected to the sliding element 56. For the sliding joint 24, this defines an interior space which houses additional components of the holding device 12.

The distal instrument holder 22 comprises a guide ball 72, which is arranged in a ball cup 74. In the embodiment according to FIG. 3, the ball cup 74 is designed as a yoke 76 or in a yoke-like manner. The ball cup 74 provides a receiving means for the guide ball 72, said receiving means having a spherically shaped surface, which is adapted to the outer surface of the guide ball 72. Two shanks 78 connect to the ball cup 74. The two shanks 78 are oriented proximally starting at the distally arranged ball cup 74.

In the embodiment, the ball cup 74 and the two shanks 78 are designed like a yoke 76. In the assembled state (cf. FIGS. 2 and 4), the shanks 78 penetrate through a slit-like recess in the cap 70. In the assembled state, a pin 80 penetrates the shanks 78 as well as the distal end of the sliding element 56 (cf. FIGS. 4 and 5). The pin 80 and the design of the slit in the cap 70 ensure a non-rotational bracing of the distal instrument holder 22 on the distal sliding element 56. In other words, the yoke-like ball cup 74 cannot be pivoted or be pivoted only imperceptibly about a longitudinal axis through the holding device 12 (cf. reference number 132 in FIG. 4).

In the embodiment according to FIG. 3, transfer elements 84, 86, 88 are arranged inside the sliding joint 24. In an illustrative embodiment, the number of transfer elements 84, 86, 88 is matched to the number of sliding elements 52, 54, 56. A proximal transfer element 84 faces the proximal base 20. A distal transfer element 88 faces the distal instrument holder 22. The middle transfer element 86 is arranged between the transfer elements 84 and 88. The transfer elements 84, 86, 88 have profile bodies 90, which are illustratively designed as tube pieces. In other words, the profile bodies 90 have a circular or annular cross-section. In the embodiment, the transfer elements 84, 86, 88 are designed as hollow cylinders. In the design according to FIG. 3, the distal transfer element 88 has a larger cross-section than the middle transfer element 86, wherein the middle transfer element 86 has a larger cross-section than the proximal transfer element 84.

In the embodiment, the sliding elements 52, 54, 56 taper from the proximal to distal end. In the embodiment, the transfer elements 84, 86, 88 taper from the distal to the proximal end.

The sliding elements 52, 54, 56 of the sliding joint 24 are translationally displaceable but coupled to each other in a non-rotational manner. The transfer elements 84, 86, 88 are arranged inside the sliding elements 52, 54, 56. The transfer elements 84, 86, 88 can be rotated at least between a first position (assigned to a released state) and a second position (assigned to a clamped state). The transfer elements 84, 86, 88 are absolutely rotatable (with respect to the surroundings or the sliding joint 24), wherein at least some of the transfer elements 84, 86, 88 can be rotated relative to each other. This will be explained in greater detail below.

Similarly to the proximal sliding element 52, the proximal transfer element 84 is coupled to the proximal base 20. In an illustrative embodiment, there is no translational movement between the base 20, the upper sliding element 52 and the proximal transfer element 84. In an illustrative embodiment, the distal transfer element 88 is coupled to the distal sliding element 56 for the purpose of carrying the movement along in a translational manner. Thus, when the sliding joint 24 is extended, the transfer elements 84, 86, 88 are also pulled apart (expanded). In the depicted embodiment, the transfer element 86 is translationally displaceable relative to the transfer element 84 and relative to the transfer element 88. The extension movement and retraction movement of the transfer elements 84, 86, 88 are adapted to the extension movement and retraction movement of the sliding elements 52, 54, 56.

In illustrative embodiments, a drive 94 is provided to selectively lock or release the holding device 12. In this way, an instrument 14, which is attached to the instrument holder 22, can be positioned and oriented in a desired direction. FIG. 3 depicts that the drive 94 comprises a motor 96 which has a housing 98 designed in a cartridge-like or casing-like manner, for example. The motor 96 is designed for illustrative purposes as an electric motor. The motor 96 is coupled to a control device (not depicted), which comprises at least one switch for activating and/or deactivating the motor. Activation may include activation in a first rotation direction or activation in a second rotation direction as needed. In other words, in an illustrative embodiment, the control device or the at least one switch has three switch positions for the drive.

In the embodiment, there is formed on the housing 98 a bearing piece 100, which secures the drive 94 to the proximal transfer element 84 (cf. also FIGS. 5 and 11). In other words, the drive 94 is supported on the housing side by the transfer element 84. The drive 94 also comprises a drive shaft 102, which in the embodiment is coupled to a tappet 104. The tappet 104 transfers a rotational drive movement of the drive 94 to the middle transfer element 86 (cf. FIGS. 5 and 11). When the drive 94 is activated, the transfer elements 84 and 86 are in this way rotated in opposite directions. The drive 94 acts via the drive shaft 102 and the tappet 104 by means of a drive torque on the transfer element 86. A reaction torque created in this way basically acts on the proximal transfer element 84 via the bearing piece 100. This results in a compact, integrated design because the drive 94 does not have to be necessarily mounted on the frame side.

The two transfer elements 86, 88 are coupled to each other in a non-rotational manner and translationally displaceable relative to each other. In other words, the two transfer elements 86, 88 jointly form a (additional) sliding joint, which however can be rotated collectively (absolutely) by the drive 94. Thus, when the drive 94 is activated, the transfer elements 86, 88 rotate in a first direction, whereas the transfer element 84 rotates in an opposite second direction. This design allows the drive 94 to not require being mounted separately on the frame in a fixed manner. However, one can conceive of holding devices with uniformly rotating transfer elements, which then have to be designed non-cylindrically as an example.

The proximal transfer element 84 and the middle transfer element 86 are coupled to each other indirectly via the drive 94 or its bearing piece 100 as well as the tappet 104, and can be displaced and rotated translationally relative to each other. The middle transfer element 86 and the distal transfer element 88 are coupled to each other translationally and non-rotationally via at least one guide 110 as well as at least one guide element 112 arranged therein. The guide 110 is, for example, an elongated hole or a guide slit. Accordingly, the guide element 112 is designed, for example, as a guide pin or bolt, which is arranged in the guide 110. Together, the guide 110 and the guide element 112 ensure translational displaceability and the non-rotational connection between the transfer element 86 and the transfer element 88. In this way, a rotational movement, which is introduced via the tappet 104 to the transfer element 86, is also transferred to the transfer element 88.

On its distal end, the distal transfer element 88 is coupled to a clamping ring 116, which forms an eccentric 118 or has eccentric contours. The clamping ring 116 is coupled non-rotationally to the transfer element 88 and is rotated jointly with it. As needed, the clamping ring acts with the inwardly-oriented eccentric 118 on the shanks 78 of the yoke-like ball cup 74 to compress the latter (cf. also FIGS. 5 and 9).

In this way, the shanks 78 of the yoke 76 can be tensioned if necessary to fix the guide ball 72 in the ball cup 74. In this way, the second joint (ball joint) 32 can be blocked or locked as needed. In an illustrative embodiment, in this state (clamped state) the guide ball 72 is connected securely to the ball cup 74 so that no pivot movements (cf. the arrows 40, 42 in FIG. 2) are possible. In another illustrative embodiment, the instrument receiving means 44 is also pretensioned so that a received instrument 14 can no longer be rotated about the instrument axis 46 (cf. also FIG. 2). In the disengaged/unlocked state (released state), the clamping ring 16 is rotated in such a manner that the eccentric 118 no longer presses the shanks 78 together. In this state, the guide ball 72 can be pivoted in the ball cup 74. If necessary, a rotation of the instrument 14 about the instrument axis 46 in the instrument receiving means 44 and, if applicable, displacement along the instrument axis 46 are made possible.

The proximal transfer element 84 is coupled at its proximal end to a connecting piece 122, which in the embodiment is designed in a disk- or cap-like manner. The connecting piece 122 is coupled non-rotationally with the transfer element 84 and is jointly rotated with it. The connecting piece 122 carries an eccentric 124, which is designed in the embodiment as a proximal extension of the connecting piece 122. In the embodiment, the eccentric 124 projects into a recess 128 in the pivot piece 64 of the proximal base 62 (cf. also FIGS. 5 and 6).

At least one plunger 126 is arranged in the recess 128 of the pivot piece 64. The eccentric 124 acts, as needed, on the at least one plunger 126 and squeezes it radially outward to immobilize (to block or to lock) the pivot piece 64 relative to the receiving means 62. The rotation movement of the eccentric 124 is initiated by the drive 94. In this way, the first joint (swivel joint) 30 can be locked (clamped state). In the disengaged/unlocked state (released state), the eccentric 124 is rotated in such a manner that the at least one plunger 126 in the recess 128 is no longer pretensioned against receiving means 62. This releases the first joint 30.

In the clamped state, however, it is also necessary to lock or block translational movements of the sliding joint 24. FIGS. 4-11 illustrate relevant designs. In the depicted embodiment, the translational movement of the sliding elements 52, 54, 56 of the sliding joint 24 corresponds to a translational movement of the transfer elements 84, 86, 88. The transfer elements 86, 88 are coupled translationally and non-rotationally to each other via at least one guide 110 and one guide element 112 engaging in the guide 110 (cf. FIG. 4). In addition, FIG. 4 shows a guide identified as 134 on the transfer element 86 for the tappet 104 of the drive 94. The tappet 104 has for example a projection (not depicted in detail) which engages in the guide 134. In this way, a translational movement is enabled between the drive 94 or its tappet 104 and the transfer element 86, and thus a translational relative movement between the transfer elements 84 and 86.

When the drive 94 is activated, the tappet 104 rotates relative to the bearing piece 100. The bearing piece 100 is coupled to the transfer element 84. The tappet 104 is coupled to the transfer element 86. In this way, a relative rotation is achieved between the transfer elements 84, 86. The transfer element 88 rotates together with the transfer element 86. Depending on the rotation direction of the drive 94, the transfer elements 86, 88 turn clockwise for example, while the transfer elements 84 simultaneously rotate in a counter-clockwise direction. A reversed allocation is also conceivable.

These rotation movements are firstly used for locking the first joint 30 and the second joint 32 (FIG. 2) as needed. However, the rotation movement can also be used to lock the sliding joint 24 as needed. FIG. 4 as well as supplementally FIG. 11 schematically indicate so-called clamping elements 138, 140, 142, 144, which clamp or release the joints 24, 30, 32 as required. In the clamped state, the joints 24, 30, 32 are locked, at least sufficiently blocked. In the released state, the joints 24, 30, 32 are disengaged or at least sufficiently movable to allow the instrument 14 to be positioned. FIG. 6 depicts a cross-section through the clamping element 138. FIG. 7 depicts a cross-section through the clamping element 140. FIG. 8 depicts a cross-section through the clamping element 142. FIG. 9 depicts a cross-section through the clamping element 144.

The proximal clamping element 138 comprises the eccentric 124, which interacts with the at least one plunger 126 to brace the pivot piece 64 and the receiving means 62 against each other. The drive force or drive torque is transferred by the drive 94 via its bearing piece 100 to the proximal transfer element 84, from the transfer element 84 to the connecting piece 122 and from the connecting piece 122 to the eccentric 124 designed as an extension, to lock the first joint 30 designed as a swivel joint. FIG. 6 depicts a release position of the proximal clamping element 138.

The distal clamping element 144 comprises the clamping ring 116, which is provided with the eccentric 118 and which acts on the shank 78 of the ball cup 74. In this way, the ball cup 74 and the guide ball 72 can be braced against each other. The drive force or drive torque is transferred from the drive 94 via its tappet 104 to the middle transfer element 86, from the middle transfer element 86 to the distal transfer element 88 and from there via the clamping ring 116 and its eccentric 118 to the shank(s) 78, to lock the second joint 32 designed as a ball joint. FIG. 9 depicts a release position of the distal clamping element 144.

At least one additional clamping element 140, 142 is provided between the proximal clamping element 138 and the distal clamping eluent 144 to lock the sliding joint 24. In the embodiment, two clamping elements 140, 142 are provided, which are arranged between the proximal clamping element 138 and the distal clamping element 144.

FIG. 5 and FIG. 11 show that the clamping elements 140, 142 are actuated via the middle transfer element 86 and the distal transfer element 88. The drive 94 is coupled via the tappet 104 to the middle transfer element 86 as well as via the guide 110 and the guide element 112 to the distal transfer element 88.

The clamping element 140 is formed on the proximal end of the middle transfer element 86. An eccentric 150 designed as an eccentric spring is formed on the proximal end region of the middle transfer element 86. FIG. 7 shows that, for example, two such eccentric springs 150 can be provided, which are arranged offset by 180°. Given a rotation (counter-clockwise in FIG. 7) of the middle transfer element 86, the eccentric springs 150 are transferred from a release position (eccentric springs 150 do not contact the proximal sliding element 52) shown in FIG. 7 into a clamping position, in which the eccentric springs 150 contact the proximal sliding element 52. The eccentric springs 150 are also assigned stops 152, 154, which define the end regions of the movement between the clamping position (stop 152) and the release position (stop 154). The stops 152, 154 are provided on the middle sliding element 54, for example.

The eccentric springs 150 also adjoin the proximal end of the middle transfer element 54 (cf. FIG. 5). When the eccentric springs 150 near the proximal end of the sliding element 54 act on the proximal sliding element 52, the result is a large usable travel path of the translational movement. The eccentric springs 150 or clamping element 140 are arranged in such a manner that a joint translational movement occurs with the middle sliding element 54 and the middle force transfer element 86, when the sliding joint 24 is extended or retracted.

The clamping element 142 is formed on the proximal end of the distal transfer element 88. An eccentric 160 designed as an eccentric spring is formed on the proximal end region of the distal transfer element 88. FIG. 8 depicts that, for example, two such eccentric springs 160 can be provided, which are arranged offset by 180°. Given a rotation (clockwise in FIG. 8) of the middle transfer element 86 and consequently the distal transfer element 88, the eccentric springs 160 are placed from a release position (eccentric springs 160) shown in FIG. 8 into a clamped position, in which the eccentric springs 160 contact the middle sliding element 54 with a certain force/pretension. Assigned to the eccentric springs 160 are also stops 162, 164, which define end regions of the movement between the clamping position (stop 162) and the release position (stop 164). The stops 162, 164 are provided on the distal sliding element 56, for example.

The eccentric springs 160 also adjoin the proximal end of the distal sliding element 56 (cf. FIG. 5). When the eccentric springs 160 close to the proximal end of the distal sliding element act on the middle sliding element 54, the result is a large usable travel path in the translational movement. The eccentric springs 160 or clamping element 142 are arranged in such a manner that a joint translational movement with the distal sliding element 56 and the distal force transfer element 88 occurs when the sliding joint 24 is extended or retracted.

The clamping elements 138, 140, 142, 144 are simultaneously controlled via the drive 94. The drive 94 can be operated in a first rotation direction to bring the clamping elements 138, 140, 142, 144 to a clamped state. The drive 94 can be operated in an opposite second rotation direction to bring the clamping elements 138, 140, 142, 144 to a released state.

It is understood that the clamping elements 138, 140, 142, 144, or at least some of the clamping elements 138, 140, 142, 144, can also be designed in other ways. In the embodiment, the clamping elements 138, 140, 142, 144 create the advantage that a plurality of degrees of freedom of movement of the holding device can be simultaneously locked or released using only one drive or only one step.

On the basis of the illustration according to FIG. 5, FIGS. 10 and 11 depict additional features of the holding device. FIG. 10 shows a broken cross-sectional view in which the depiction of the transfer elements 84, 86, 88 and the drive 94 was intentionally omitted. FIG. 11 shows a broken cross-sectional view in which the depiction of sliding elements 52, 54, 56 of sliding joint 24 was intentionally omitted. In FIGS. 10 and 11, the clamping elements 138, 140, 142, 144 are indicated by dashed boxes to show that other designs are also conceivable to lock or release the involved elements as needed.

Figure 12:
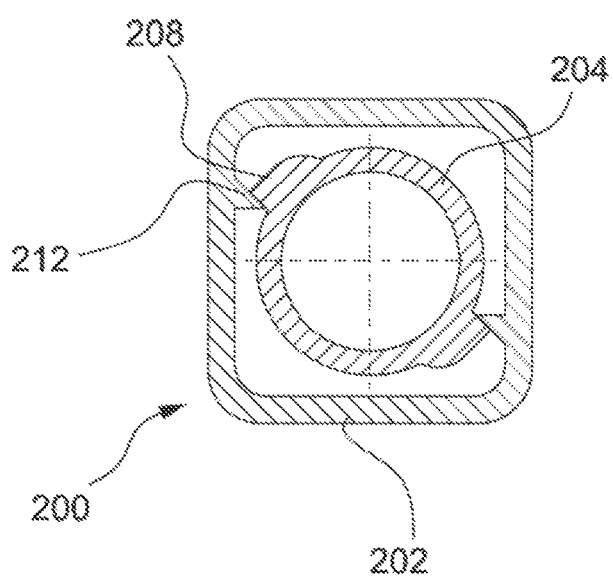
FIG. 12 depicts a schematically cut frontal view to show an illustrative embodiment of a clamping element in a released state.
Figure 13:
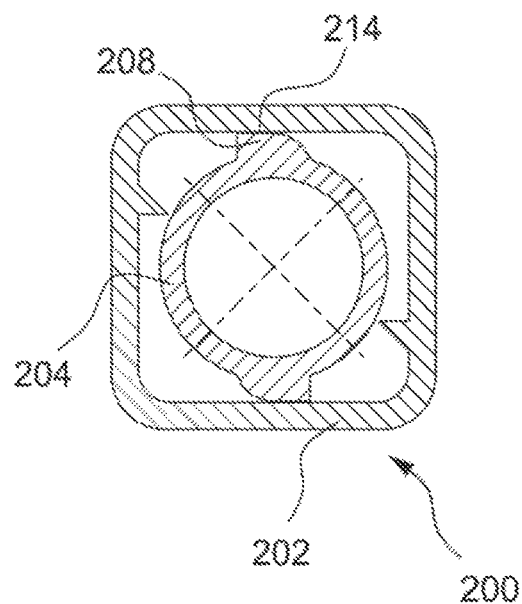
FIG. 13 depicts another view illustrating the clamping element according to FIG. 12, as an illustration of a clamped state.

In this context, FIGS. 12 and 13 depict another illustrative embodiment of a clamping element 200. As an example, the clamping element 200 may be provided as an alternative to one of the clamping elements 140, 142. FIG. 12 depicts a released state. FIG. 13 depicts a clamped state of the clamping element 200.

The clamping element 200 is formed between a sliding element 202 (cf. sliding elements 52, 54, 56) and a transfer element 204 (cf. the transfer elements 84, 86, 88). The clamping element 200 comprises an eccentric contour 208, which comprises, for example purposes, two projections offset by 180° on the transfer element 204. The eccentric contour 208 can also be referred to as an eccentric cam. In the release position according to FIG. 12, the eccentric contour 208 abuts a stop 212, which is assigned to the sliding element 202.

By a rotational movement of the transfer element 204 with the eccentric contours 208 (clockwise in the embodiment), the clamping element 200 is placed in the clamping state. In FIG. 13, the eccentric contours 208 form a stop 214 for the clamped state by means of a flush or generally flush contact on the sliding element 202. It is understood that the stop 214 can also be designed in other ways and can in particular comprise raised design elements on the sliding element 202.

The raised eccentric contours 208 may be designed as sufficiently stiff contours. In this way, the holding force in the clamped state arises primarily from the resulting static friction. However, the raised eccentric contours 208 can also be formed at least in a partially elastic (flexible) manner. In this way, the holding force in the clamped state results at least partially from a spring force of the eccentric contours 208. Desired properties of the eccentric contours 208 can be influenced, for example, by the choice of material.

Supplementing FIGS. 5-11, FIGS. 12 and 13 depict that the transition between the released state and the clamped state is made possible by eccentric contours 208 on the one hand, and on the other by the intentionally different cross-sectional form of the sliding elements 202 and the transfer elements 204. In such an arrangement, a relative rotation between the sliding elements 202 and the transfer element 204 at a manageable pivot angle (approximately 45° or less) is sufficient to effect the desired clamping or release. This is not to be understood as being restrictive. It is understood that particularly the sliding elements 202 can have other cross-sectional profiles than square (quadratic cross-section or rectangular cross-section).

Figure 14:
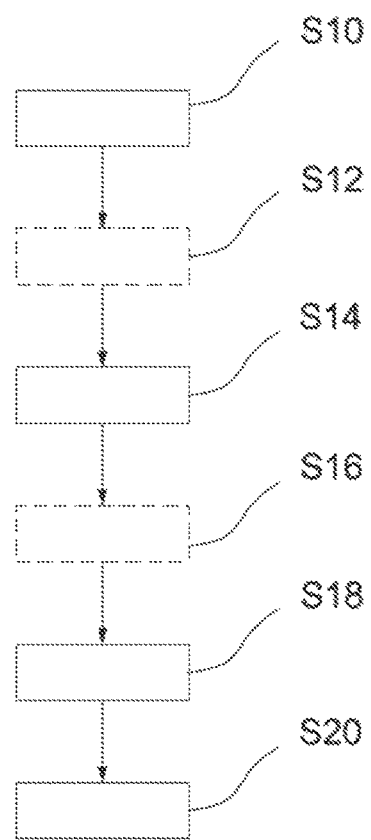
FIG. 14 depicts a flow chart to show an illustrative embodiment of a method for positioning a medical instrument.

With reference to FIG. 14, a schematic, highly simplified flow chart depicts an illustrative embodiment of a method for positioning a medical instrument. The method is suited for medical instruments which are designed for observing the body of a patient from outside the body and for which no access opening to the body is thus required.

The method comprises a step S10, which comprises providing a holding device according to at least one of the embodiments described herein. An optional step S12 may follow, which involves fastening the holding device to a frame in the surroundings of a patient support platform. This can be a temporary or a permanent fastening.

A further step S14 relates to fastening a medical instrument to an instrument holder of the holding device. The instrument is an observation instrument, for example. An optional step S16 may follow, which is then required when the clamping elements of the holding device are in a clamped state. In step S16, some or all of the clamping elements are placed in the released state to enable degrees of freedom of movement of the holding device.

Positioning the instrument takes place in step S18. This relates to placing the instrument at a certain location (for example at a certain coordinate in a plane) on the one hand and on the other at a desired orientation of the instrument. The first-mentioned placement uses, for example, the rotational degrees of freedom of the swivel joint as well as the translational degree of freedom of the sliding joint of the holding device. The orientation may pertain to a pivot orientation of the instrument by using the ball joint of the holding device. Furthermore, the orientation can pertain to a rotation of the instrument about its longitudinal axis and possibly a movement along the longitudinal axis.

When the device is placed in the desired position and orientation, the holding device can be locked in a subsequent step S20 by clamping elements of the holding device being placed in a clamped state. In this way, the instrument is sufficiently fixed and positionally secured. A medical procedure involving use of the instrument may follow.

In the event of repositioning or changing the instrument, at least some steps of the method can be run through again. The simultaneous activation or deactivation of the clamping elements, at least in illustrative embodiments, is advantageous, as a result of which the entire holding device can be placed in the released state or the clamped state with only one action, if needed. The actual positioning and orientation of the instrument can take place manually. Actuating the clamping elements may take place by means of a drive, for example a motor drive.

It is understood that the aforementioned features and those still to be explained below can be used not only in the respective indicated combination but also in other combinations or individually without departing from the scope of the present disclosure.

The disclosure relates to a holding device 12 for medical instruments 14, having a proximal base 20 for mounting on a frame 16 which comprises a first joint 30, a distal instrument holder 22 which comprises a second joint 32, at least two sliding elements 52, 54, 58 between the base 20 and the instrument holder 22, and at least two clamping elements 138, 140, 142, 144, which can be actuated by at least one transfer element 84, 86, 88, which can be operated jointly in a clamped state and a released state, and which are designed to lock joints of the holding device 12 in the clamped state, wherein the at least two sliding elements 52, 54, 58 form a sliding joint 24 and can be displaced translationally relative to each other along a longitudinal axis 132, and wherein the at least two sliding elements 52, 54, 58 are telescopable relative to each other and coupled to each other in a non-rotational manner. The disclosure also relates to a medical system, a use of a holding device, as well as a method for positioning a medical instrument.

The invention claimed is:

1. A holding device for medical instruments, comprising:
   a proximal base for mounting to a frame, said base comprising a first joint,
   a distal instrument holder which comprises a second joint,
   at least two sliding elements between the base and the instrument holder, and
   at least two clamping elements which can be actuated by at least one transfer element, which can be jointly operated in a clamped state and a released state, and which are designed to lock joints of the holding device in the clamped state,
   wherein:
   the at least two sliding elements form a sliding joint and can be displaced translationally relative to each other along a longitudinal axis,
   the at least two sliding elements are telescopable relative to each other and are coupled to each other in a non-rotational manner, a common drive is provided for the at least two clamping elements which simultaneously actuates the at least two clamping elements, and the drive comprises a drive shaft which interacts with at least one of the at least two clamping elements, wherein the drive also has a bearing which, when driving the drive shaft, absorbs a resulting counter-torque, and the bearing interacts with at least one other clamping element.

2. The holding device according to claim 1, wherein the first joint is a swivel joint, and/or the second joint is a ball joint.

3. The holding device according to claim 1, wherein the first joint comprises a receiver and a pivot piece, which jointly define a pivot axis, wherein the first joint is assigned a proximal clamping element which blocks or locks the first joint in a clamped state as needed.

4. The holding device according to claim 1, wherein the second joint comprises a guide ball and a ball cup, wherein the guide ball has an instrument receiver adapted to receive the medical instruments, and wherein the second joint is assigned a distal clamping element which blocks or locks the second joint in the clamped state as needed.

5. The holding device according to claim 4, wherein the ball cup is a yoke-like ball cup and the distal clamping element acts on the yoke-like ball cup to fix the guide ball relative to the ball cup.

6. The holding device according to claim 1, wherein the common drive is one single drive.

7. The holding device according to claim 2, wherein the medical instruments are endoscopic instruments.

8. The holding device according to claim 1, wherein the drive shaft is oriented parallel to the longitudinal axis, and wherein the bearing is coupled to a proximal clamping element that is assigned to the first joint.

9. The holding device according to claim 1, wherein the drive is coupled to at least two telescopable transfer elements, wherein the number of transfer elements is adapted to the number of sliding elements, and wherein the at least two transfer elements transfer a rotation movement induced by the drive to place the at least two clamping elements into the clamped state or the released state.

10. The holding device according to claim 1, wherein the drive is coupled to two adjoining transfer elements in such a manner that the adjoining transfer elements are rotated in opposite directions when the drive moves.

11. The holding device according to claim 1, wherein the sliding elements and the at least one transfer element is a hollow profile body, wherein the at least one transfer element is arranged inside the sliding elements, and wherein the drive has a cartridge-like housing that is non-rotationally coupled to one of the at least one transfer element.

12. The holding device according to claim 1, wherein three or more transfer elements are provided, of which at least two adjoining transfer elements are coupled non-rotationally to each other and can be displaced translationally relative to each other.

13. The holding device according to claim 1, comprising at least three sliding elements which form the sliding joint and are telescopable, wherein, starting at the proximal base and going toward the distal instrument holder, cross-sectional profiles of the at least three sliding elements are graduated and become smaller.

14. The holding device according to claim 1, wherein the at least two sliding elements have a box profile, and wherein the box profiles of the sliding elements are adapted to each other in such a manner that the sliding elements are telescopable along the longitudinal axis and coupled to each other in a non-rotational manner.

15. The holding device according to claim 1, wherein a clamping element is provided between two adjacent sliding elements.

16. The holding device according to claim 1, comprising:
exactly three telescopable sliding elements comprising a proximal sliding element, a middle sliding element and a distal sliding element, which form the sliding joint, wherein the three sliding elements are coupled to each other in a non-rotational manner,
exactly three telescopable transfer elements comprising a proximal transfer element, a middle transfer element and a distal transfer element, which are arranged inside the three sliding elements,
a swivel joint, which forms the first joint at the proximal base,
a ball joint, which forms the second joint at the distal instrument holder,
a first clamping element, which is assigned to the swivel joint and is arranged between the proximal transfer element and the swivel joint,
a second clamping element, which is arranged between the middle transfer element and the proximal sliding element,
a third clamping element, which is arranged between the distal transfer element and the middle sliding element,
a fourth clamping element, which is assigned to the ball joint and is arranged between the distal transfer element and the ball joint,
wherein the four clamping elements in the clamped state lock the swivel joint, the sliding joint and the ball joint,
wherein the four clamping elements can be jointly activated or deactivated, and
wherein the four clamping elements can be controlled via the common drive to simultaneously lock or release the swivel joint, the sliding joint and the ball joint.

17. A holding device for medical instruments, comprising:
a proximal base for mounting to a frame, said base comprising a first joint,
a distal instrument holder which comprises a second joint,
at least two sliding elements between the base and the instrument holder, and
at least two clamping elements which can be actuated by at least one transfer element, which can be jointly operated in a clamped state and a released state, and which are designed to lock joints of the holding device in the clamped state,
wherein:
the at least two sliding elements form a sliding joint and can be displaced translationally relative to each other along a longitudinal axis,
the at least two sliding elements are telescopable relative to each other and are coupled to each other in a non-rotational manner, and
at least the clamping elements assigned to the at least two sliding elements can be rotationally actuated and the at least two sliding elements clamp with the at least one transfer element in a given translational position.

18. The holding device according to claim 17, wherein at least one of the clamping elements has an eccentric, wherein at least one eccentric is designed as a spring eccentric and/or has eccentric contours, and wherein, given a relative rotation between at least one transfer element and the sliding elements, the eccentric brings about a force-fit locking.

19. A method for positioning a medical instrument comprising:

providing a holding device, the holding device comprising:
- a proximal base for mounting to a frame, said base comprising a first joint,
- a distal instrument holder which comprises a second joint,
- at least two sliding elements between the base and the instrument holder, and
- at least two clamping elements which can be actuated by at least one transfer element, which can be jointly operated in a clamped state and a released state, and which are designed to lock joints of the holding device in the clamped state, wherein:
- the at least two sliding elements form a sliding joint and can be displaced translationally relative to each other along a longitudinal axis,
- the at least two sliding elements are telescopable relative to each other and are coupled to each other in a non-rotational manner,
- a common drive is provided for the at east two clamping elements which simultaneously actuates the at least two clamping elements, and
- the drive comprises a drive shaft which interacts with at least one of the at least two clamping elements, wherein the drive also has a bearing which, when driving the drive shaft, absorbs a resulting counter-torque, and the bearing interacts with at least one other clamping element, fastening the medical instrument to the distal instrument holder, positioning the holding device with the instrument with the at least two clamping elements in the released state, and locking the holding device with the at least two clamping elements in the clamped state.

* * * * *